April 28, 1942. B. D. DRAIN Plant Pat. 512
RED RASPBERRY
Filed Nov. 1, 1940
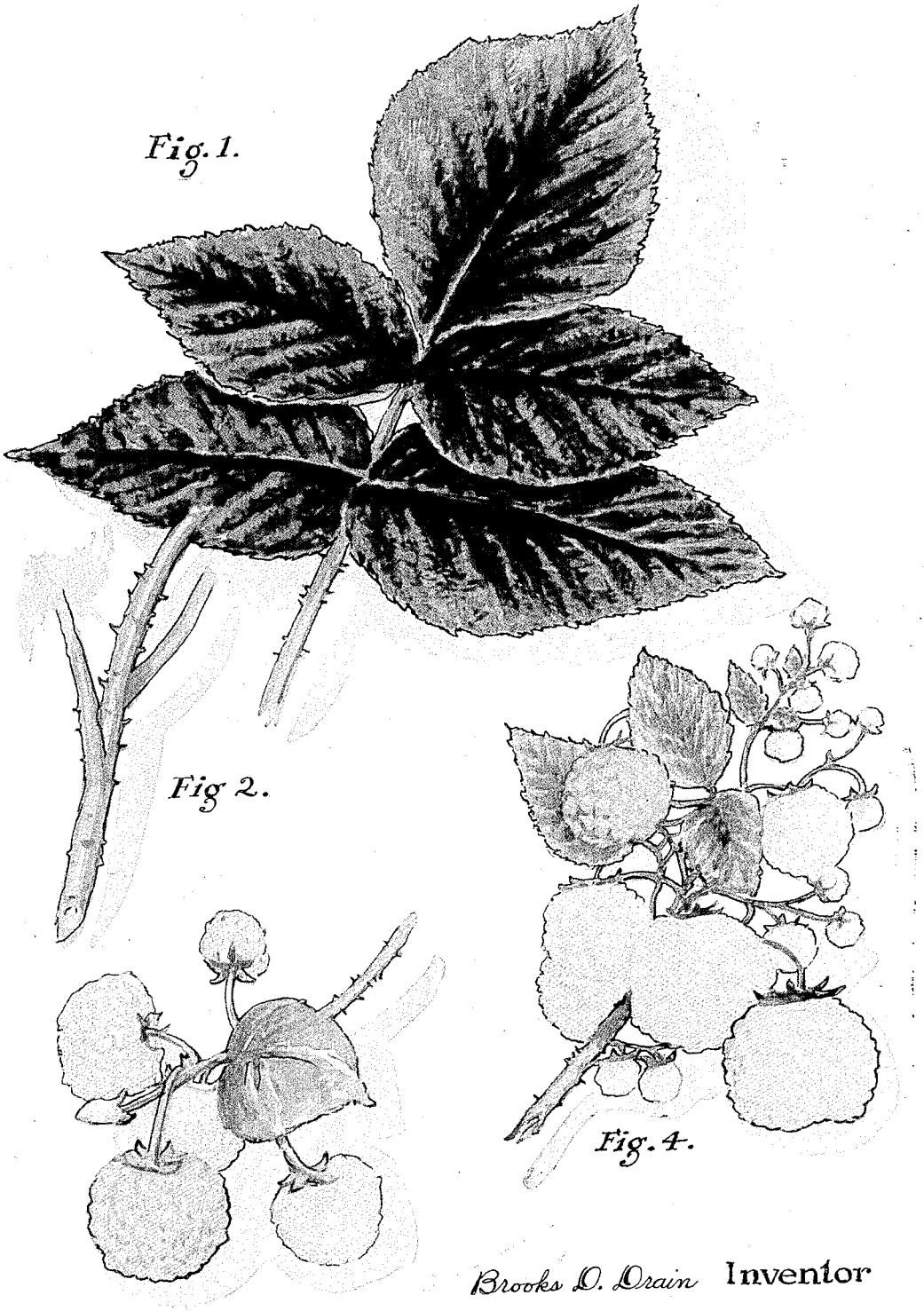
Brooks D. Drain Inventor
By Cameron, Kerkam & Sutton Attorneys Patented Apr. 28, 1942

Plant Pat. 512

UNITED STATES PATENT OFFICE

512

RED RASPBERRY

Brooks D. Drain, Knoxville, Tenn., assignor to The University of Tennessee Research Corporation, Knoxville, Tenn., a corporation of Tennessee Application November 1, 1940, Serial No. 363,934

1 Claim. (Cl. 47—62)

This invention pertains to a new and distinct variety of red raspberry produced by the artificial pollination of Tennessee Seedling 181 (Van Fleet×Latham) with the pollen of the Lloyd George red raspberry.

The object of the invention is to produce a red raspberry plant which is sturdy, adapted to soils and climates similar to that of Tennessee and which is more or less resistant to the foliage and systemic diseases of red raspberries. The new variety of raspberry has all of the desirable characteristics of the fruit and plant of the parent varieties with respect to commercial quality. This includes ever-bearing, large production of fruit, good flavor, large sized and bright colored red raspberries which are easily handled.

Referring to the drawing,

Fig. 1 is a view of a leaf;

Fig. 2 is a view of a plant stalk showing color, habits of growth and the sturdy nature of the plant;

Fig. 3 shows a cluster of berries as produced in late spring and early summer;

Fig. 4 shows a fruiting cluster as produced in September and October;

The ripe berries in both Figs. 3 and 4 illustrate color and shape of fruit.

The new variety was propagated and asexually reproduced in the following manner: Pollen of the Lloyd George red raspberry was inserted into the blossom of the Tennessee Seedling 181 (Van Fleet×Latham), the pollen producing parts of the blossom of the latter variety having been first removed. The pollinated blossoms were then suitably protected to prevent reception of the pollen of any other plant. The flowers were allowed to develop into fruit and the seeds from this fruit were then planted and allowed to sprout. When the plants had grown to sufficient size they were transplanted and allowed to fruit in the field. At about the time these plants were fruiting each individual plant was examined for freedom from disease and desirable growth habits. At the same time the fruit was tasted and examined for desirable fruit characteristics.

This variety is the best among a large number of seedling and was saved and propagated asexually using root cuttings and sucker plants. All of the plants which are now growing have come from this original plant. Tennessee Seedling 181 (Van Fleet×Latham) was originated by the inventor in a similar manner.

The new variety of raspberry differs in numerous respects from known varieties. As a basis of comparison, I have taken the Ranere (St. Regis) variety. The new variety differs from the Ranere as follows: The plants of the new variety are full and vigorous, those of the Ranere are only medium in height and vigor. The canes of the new variety are stocky, with spines numerous toward the base and few toward the tip; those of the Ranere are slender with spines more numerous toward the tip. The fruit of the new variety starts to ripen in the spring several days after that of the Ranere. The berries of the new variety are large in size, the berries of the Ranere are small in size. The fruit of the new variety is a darker red in color than that of the Ranere. The fruit of the new variety is tart in flavor, becoming subacid when fully ripe, the flavor of the fruit of the Ranere is mild and insipid. The new variety, other conditions equal, yields a much larger crop than the Ranere, in the fall of the year.

The characteristics of the variety are as follows: From 1 to 15 canes with numerous prickles or thorns grow up from each plant. These canes are sturdy and upright in habits of growth with more or less side branching. Heavy crops of fruit tend to bend the canes to the ground, necessitating some means of support. A fall crop ripens in September and October and is produced toward the tips of the canes. A second crop is produced on these canes in late May and June of the following year. New canes grow from or near the crown of the plant annually. A given plant is usually surrounded by sucker plants. The bark of the canes is usually greenish in color. No systemic diseases have developed on this variety up to the present time.

The leaves are flat, 3-lobed, of medium size, and their edges have medium sized serrations. Unsprayed foliage has usually developed a slight amount of leaf spot. Most leaves remain on the plants until injured by cold in the autumn.

The berries produced by this plant are hemispherical in shape and large in size, very large specimens sometimes attaining a diameter of one inch. They are medium red in color, subacid and of good flavor. Up to the present time the plants have produced large crops in September and October and a medium crop in May and June. Plants of this variety are now being grown in various sections of Tennessee and at a few agricultural experiment stations.

Further information:

Plants: Tall. Vigorous. Upright.

*Prop. by suckers.*—Hardy. Very productive.

*Suckers.*—Numerous.

*Canes.*—Stocky. Brown. Gray. Dull. Glaucous. Without glandular tips. *Spines or prickles.*—Slender. Weak. Straight. Sharp. Medium number. Numerous toward base, few at tips. *Color.*—reddish brown.

*Leaflets.*—Number—usually 3, occasionally 5. Large. Ovate. Upper surface—dark green. Dull. Roughened. Lower surface—greenish. Pubescent below. *Margin*—crenate. Uneven. Double series. Jagged. *Petiole*—medium length. Medium thickness. Spiny few. Pubescent—glabrous.

*Flowers.*—Date of bloom: spring crop—April 28 to May 23, 1941. Fall crop—during August and September season—early. medium. White. Spines on the sepals.

Fruit: Early.

*Date of ripening.*—Spring crop—at Knoxville, Tennessee, May 23 to July 12, 1938, June 14 to July 22, 1940, June 4 to July 12, 1940. Fall crop—at Knoxville, Tennessee, September 1 to October 31, 1939, September 11 to November 8, 1940.

*Length of season.*—Spring crop 5 to 6 weeks. Fall crop about 8 weeks.

*Borne how.*—Clusters averaging 5 to 6 berries each.

*Keeping quality.*—Good.

*Shipping quality.*—Medium to good.

*Picking quality.*—Good.

*Adherence.*—Strong. Large. Medium uniform. Drops to some extent in size. Regular. Medium length. Roundish.

*Bloom.*—White.

*Styles.*—Medium.

*Drupes.*—Large. Medium in number. Coherence.—medium. Medium red. R4/10 becomes R4/8 when fully ripe. Overripe berries are R3/10, according to Munsell's Book of Color, published by Munsell Color Co., Inc., 1929. Glossy. Juicy. Tender. Medium in firmness. Sprightly. Sour, becoming subacid when fully ripe. Medium-flavored. *Quality*—Good.

*Use.*—Dessert. Kitchen. Market. Home.

*Desirability.*—Home use and local markets. Makes a good frozen pack for locker plants.

*Classification*

Red raspberry hybrid of *Rubus knutzeanus* (an Oriental species), *Rubus idaeus strigosus* (an American species) and *Rubus idaeus vulgatus* (a European species).

What is claimed is:

The red raspberry substantially as herein disclosed, characterized by ever-bearing, adaptation to a soil and climate similar to that of Tennessee and prolific fruiting.

BROOKS D. DRAIN.